(12) United States Patent
Gerlach et al.

(10) Patent No.: US 7,034,018 B2
(45) Date of Patent: Apr. 25, 2006

(54) SUBSTITUTED PYRROLE MANNICH BASES TO COMBAT PAIN AND ALLERGIC REACTIONS

(75) Inventors: Matthias Gerlach, Brachttal (DE); Corinna Maul, Aachen (DE)

(73) Assignee: Gruenenthal GmbH, Aachen (DE)

( * ) Notice: Subject to any disclaimer, the term of this patent is extended or adjusted under 35 U.S.C. 154(b) by 304 days.

(21) Appl. No.: 10/168,964

(22) PCT Filed: Dec. 20, 2000

(86) PCT No.: PCT/EP00/12976

§ 371 (c)(1),
(2), (4) Date: Jun. 25, 2002

(87) PCT Pub. No.: WO01/47878

PCT Pub. Date: Jul. 5, 2001

(65) Prior Publication Data

US 2003/0023100 A1 Jan. 30, 2003

(30) Foreign Application Priority Data

Dec. 27, 1999 (DE) ........................ 199 63 174

(51) Int. Cl.
*A61K 31/535* (2006.01)
*C07D 207/00* (2006.01)

(52) U.S. Cl. .................... 514/231.5; 514/326; 514/427; 544/141; 546/208; 548/517; 548/530; 548/542; 548/543; 548/566

(58) Field of Classification Search ................ 548/532, 548/542, 543; 514/423, 424
See application file for complete search history.

(56) References Cited

U.S. PATENT DOCUMENTS 5,935,990 A    8/1999   Khanna et al.

FOREIGN PATENT DOCUMENTS

| EP | 0 035 775 | 9/1981 |
| EP | 0 038 536 | 10/1981 |
| WO | WO 94/03426 | 2/1994 |
| WO | WO 95/16674 | 6/1995 |

OTHER PUBLICATIONS

Muchowski et al Synthetic Communications 1987, 17 (7), pp. 863–875, CAS Abstract Only.*
B. L. Bray, et al., Helvetica Chimica Acta, vol. 71, No. 6, pp. 2053–2057, "Lithiated Azafulvenes by Halogen/Metal Interchange of Brominated 6–(Diisopropylamino)–1–Azafulvene Derivatives. Novel Synthesis of 5–Mono–and 4,5–Disubstituted 1H–Pyrrole–2–Carbaldehydes", 1988.
J. M. Muchowski, et al., Chemical Abstracts, vol. 108, No. 37560g, p. 37552, "Synthesis of N–Unsubstituted α–Alkylated Pyrrol–2–Acetonitriles", 1988.
H. J. Falbe, et al., Rompp–Lexikon Chemie, pp. 1032–1033, 1997.
A.K. Sheinkman et al.: "Reaction of indole with N–acylimmonium salts in situ" Database Chemabs [Online], Chemical Abstracts Service, Columbus, Ohio, U.S. accession No. 85:46297.
M. Tramontini et al.: "Further advances in the chemistry of mannich bases" Tetrahedron, vol. 46, pp. 1791–1837 1990.

* cited by examiner

*Primary Examiner*—Kamal A. Saeed
(74) *Attorney, Agent, or Firm*—Oblon, Spivak, McClelland, Maier & Neustadt, P.C.

(57) ABSTRACT

The invention relates to substituted pyrrole Mannich bases of general formula (I), wherein $R^1$=H, a $C_{1-10}$-alkyl-, aryl, a heteroaryl- or an aryl, heteroaryl-, CN, Br—, Cl or OH radical bound by a $C_{1-6}$ alkylene group, $R^2$=CH($R^4$)N($R^5$)($R^6$), R3, R3', R3" identically or individually represent H, F, Cl, Br, $CF_3$, CN, $NO_2$, $SO_2NH_2$, $NHR^7$, $SR^8$, $OR^9$, CO($OR^{10}$), $CH^2CO(OR^{11})$, $COR^{15}$, a $C_{1-10}$-alkyl-, aryl-, heteroaryl-aryl radical or a heteroalkyl radical bound by a $C_{1-6}$ alkylene group, $R^4$=an unsubstituted phenyl radical or a phenyl radical substituted at least with $C_{1-4}$ alkyl, $C_{1-3}$-alkoxy-, halogen-, a method for the production of the above-mentioned compounds, medicaments containing said compounds, and the use of said compounds in the production of medicaments. Said active ingredients are particularly suitable for pain therapy, and for treating inflammatory and allergic reactions, drug or alcohol abuse, diarrhoea, gastritis, ulcers, cardiovascular diseases, urinary incontinence, depressions, states of shock, migranes, narcolepsy, overweight, asthma, glaucoma, hyperkinetic syndrome, lack of drive, bulimia, anorexia, catalepsia, anxiolysis increasing vigilance and/or increasing libido.

93 Claims, 2 Drawing Sheets

SUBSTITUTED PYRROLE MANNICH BASES TO COMBAT PAIN AND ALLERGIC REACTIONS

Figure 1:
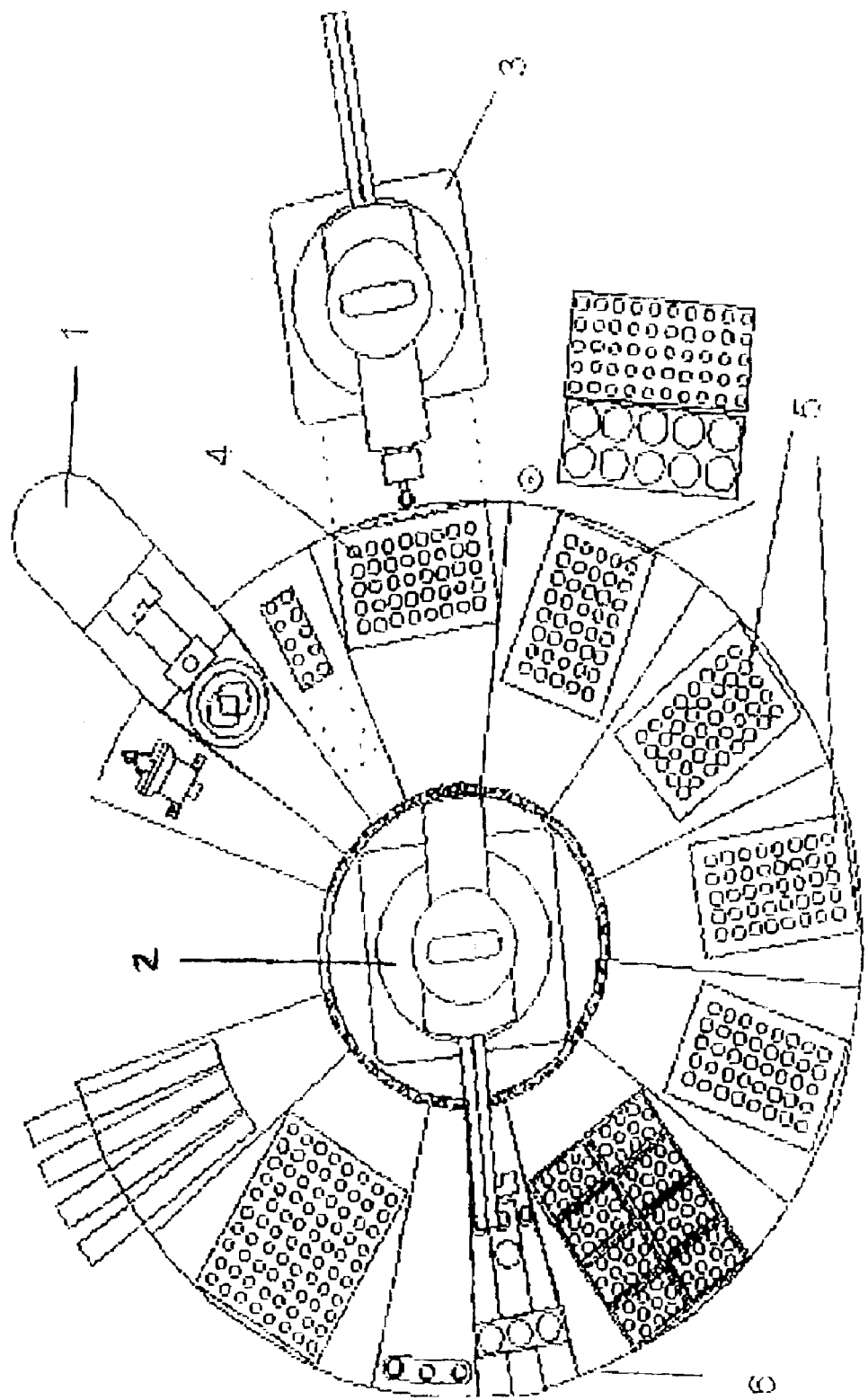

The invention relates to substituted pyrrole Mannich bases, processes for their preparation, medicaments comprising these compounds and the use of these compounds for the preparation of medicaments.

Pain is one of the basic clinical symptoms. There is a worldwide need for effective pain treatments. The urgent need for action for target-orientated treatment of chronic and non-chronic states of pain appropriate for the patient, by which is to be understood successful and satisfactory pain treatment for the patient, is documented in the large number of scientific works which have been published in the field of applied analgesia and basic research in nociception in recent years.

Conventional opioids, such as e.g. morphine, are effective in the treatment of severe to very severe pain. However, they have as undesirable concomitant symptoms, inter alia, respiratory depression, vomiting, sedation, constipation and development of tolerance.

Tramadol hydrochloride—(1RS,2RS)-2-[(dimethylamino)methyl]-1-(3-methoxyphenyl)-cyclohexanol—occupies a special position among analgesics having an action on the central nervous system, since this active compound brings about potent inhibition of pain without the side effects known of opioids (J. Pharmacol. Exptl. Ther. 267, 33 (1993)). Research is being conducted worldwide into further pain-inhibiting agents.

The object of the present invention was therefore to provide new compounds which are suitable in particular as active compounds in medicaments.

These active compounds should be suitable in particular for pain treatment and for treatment of inflammatory and allergic reactions, drug and/or alcohol abuse, diarrhoea, gastritis, ulcers, cardiovascular diseases, urinary incontinence, depression, states of shock, migraines, narcolepsy, excess weight, asthma, glaucoma, hyperkinetic syndrome, lack of drive, bulimia, anorexia, catalepsy, for anxiolysis, for increasing vigilance and/or for increasing libido.

This object is achieved according to the invention by providing substituted pyrrole Mannich bases of the following general formula I which have a pronounced analgesic action, in particular also on chronic pain, and which moreover are suitable for treatment of inflammatory and allergic reactions, drug and/or alcohol abuse, diarrhoea, gastritis, ulcers, cardiovascular diseases, urinary incontinence, depression, states of shock, migraines, narcolepsy, excess weight, asthma, glaucoma, hyperkinetic syndrome, lack of drive, bulimia, anorexia, catalepsy, for anxiolysis, for increasing vigilance and/or for increasing libido.

The present invention therefore relates to substituted pyrrole Mannich bases of the general formula I

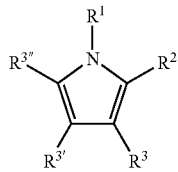

I wherein $R^1$=H, a $C_{1-10}$-alkyl, an aryl or a heteroaryl radical or an aryl, heteroaryl, CN, Br, Cl or OH radical bonded via a $C_{1-6}$-alkylene group, preferably a $C_{1-6}$-alkyl radical, a phenyl, furoyl, thiophene or pyridine radical which is unsubstituted or at least monosubstituted by F, Cl, Br, $NH_2$, $NO_2$, $NH_2$—(C=S) or COOH, or an aryl, CN, Br, Cl or OH radical bonded via a $C_{1-3}$-alkylene group, particularly preferably a phenyl or pyridine radical which is unsubstituted or at least monosubstituted by F or $NH_2$—(C=S), $R^2$=CH($R^4$)N($R^5$)($R^6$), $R^3$, $R^{3'}$, $R^{3''}$ are identical or different and=H, F, Cl, Br, $CF_3$, CN, $NO_2$, $SO_2NH_2$, $NHR^7$, $SR^8$, $OR^9$, CO($OR^{10}$), $CH_2CO(OR^{11})$, $COR^{15}$, a $C_{1-10}$-alkyl, an aryl or a heteroaryl radical or an aryl or heteroaryl radical bonded via a $C_{1-6}$-alkylene group, preferably=H, a $C_{1-6}$-alkyl radical or an aryl radical bonded via a $C_{1-2}$-alkylene group, particularly preferably=H, $R^4$=an unsubstituted phenyl radical or a phenyl radical which is at least monosubstituted by $C_{1-4}$-alkyl, $C_{1-3}$-alkoxy, halogen, $CF_3$, CN, O-phenyl or OH, preferably an unsubstituted phenyl radical or a phenyl radical which is at least monosubstituted by methyl, tert-butyl, methoxy, F, Cl, Br or $CF_3$, particularly preferably an unsubstituted phenyl radical or a 2-methoxy-phenyl, 3-methoxy-phenyl, 4-methoxy-phenyl, 2-methyl-phenyl, 3-methyl-phenyl, 4-methyl-phenyl, 2-tert-butyl-phenyl, 3-tert-butyl-phenyl, 4-tert-butyl-phenyl, 2-fluoro-phenyl, 3-fluoro-phenyl, 4-fluoro-phenyl, 2-chloro-phenyl, 3-chloro-phenyl, 4-chloro-phenyl, 2-bromo-phenyl, 3-bromo-phenyl, 4-bromo-phenyl, 5-bromo-2-fluoro-phenyl, 2-chloro-4-fluoro-phenyl, 2-chloro-5-fluoro-phenyl, 2-chloro-6-fluoro-phenyl, 4-bromo-2-fluoro-phenyl, 3-bromo-4-fluoro-phenyl, 3-bromo-2-fluoro-phenyl, 2,3-dichloro-phenyl, 2,4-dichloro-phenyl, 2,5-dichlorophenyl, 3,4-dichloro-phenyl, 2,3-dimethyl-phenyl, 2,4-dimethyl-phenyl, 2,5-dimethylphenyl, 2,3-dimethoxy-phenyl, 2,4-dimethoxy-phenyl, 2,5-dimethoxy-phenyl, 3,4-dimethoxy-phenyl, 3,4,5-trimethoxy-phenyl, 2-trifluoromethyl-phenyl, 3-trifluoromethyl-phenyl or 4-trifluoromethyl-phenyl radical, very particularly preferably an unsubstituted phenyl radical, $R^5$, $R^6$ are identical or different and denote a branched or unbranched, saturated or unsaturated, unsubstituted or at least monosubstituted $C_{1-6}$-alkyl radical or an unsubstituted or at least monosubstituted phenyl, benzyl or phenethyl radical, preferably a saturated, unsubstituted or at least monosubstituted $C_{1-6}$-alkyl radical, particularly preferably a $CH_3$ radical, or $R^5$ and $R^6$ together denote $(CH_2)_n$, where n=an integer from 3 to 6, or $(CH_2)_2O(CH_2)_2$, preferably $(CH_2)_n$, where n=4 or 5, $R^7$=H, $COR^{12}$, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^8$=H, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^9$=H, $COR^{13}$, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^{10}$=H, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^{11}$=H, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^{12}$=a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^{13}$=a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^{14}$=H, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^{15}$=NHNH$_2$, NHR$^{14}$, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, and/or their racemates, enantiomers or diastereomers and/or corresponding bases and/or corresponding salts of physiologically tolerated acids, excluding the racemate of the compound of the general formula I in which the radicals $R^1$, $R^3$, $R^{3'}$ and $R^{3''}$ each=H, the radical $R^2$=CH($R^4$)N($R^5$)($R^6$), the radical $R^4$ denotes a phenyl radical and the radicals $R^5$ and $R^6$ each=CH$_3$.

Alkyl radicals are preferably understood as hydrocarbon radicals which are at least monosubstituted by halogen, OH, CN or CF$_3$, particularly preferably by F, Cl, Br or OH. If these contain more than one substituent, these substituents can be identical or different. The alkyl radicals can be branched, unbranched or cyclic. The alkyl radicals methyl, ethyl, propyl, 1-methylethyl, butyl, 1-methylpropyl, 2-methylpropyl, 1,1-dimethylpropyl, 1,2-dimethylpropyl, 2,2-dimethylpropyl, hexyl, 1-methylpentyl, heptyl, nonyl or decanyl are particularly preferred.

An aryl radical is preferably understood as phenyl or naphthyl radicals which are at least monosubstituted by an OH, a halogen, preferably F, Br or Cl, a CF$_3$, a CN, a $C_{1-6}$-alkyl, a $C_{1-6}$-alkoxy or a phenyl radical. The unsubstituted or substituted phenyl radicals can also be fused with further rings. The aryl radicals 2-, 3- and 4-bromophenyl, 4-bromo-2-fluorophenyl, 5-bromo-2-fluorophenyl, 3-bromo-4-fluorophenyl, 4-tert-butylphenyl, 2-chloro-4-fluorophenyl, 2-chloro-6-fluorophenyl, 4-cyanophenyl, 2,3-dichlorophenyl, 2,4-dichlorophenyl, 2,6-dichlorophenyl, 3,4-dichlorophenyl, 2,3-dimethoxyphenyl, 3,4-dimethoxyphenyl, 2,4-dimethylphenyl, 2,5-dimethylphenyl, 2-, 3- and 4-fluorophenyl, 2-methoxyphenyl, 2-, 3- and 4-methylphenyl, 3-phenoxyphenyl, 2- and 4-trifluoromethylphenyl or 3,4,5-trimethoxyphenyl are particularly preferred.

A heteroaryl radical is understood as aromatic compounds which have at least one heteroatom, preferably nitrogen and/or oxygen and/or sulfur, particularly preferably nitrogen and/or oxygen, and which can preferably be substituted by a halogen, a CF$_3$, a CN or an OH radical. The heteroaryl radical is particularly preferably a substituted or unsubstituted pyrrolyl, furfuryl, pyridine or thiophene radical.

The following substituted pyrrole Mannich bases are particularly preferred:

4-[(2-methoxyphenyl)-(1-phenyl-1H-pyrrol-2-yl)-methyl]-morpholine
4-[[1-(2-fluorophenyl)-1H-pyrrol-2-yl]-(2-methoxyphenyl)-methyl]-morpholine
1-[(1-furan-2-yl-1H-pyrrol-2-yl)-(2-methoxyphenyl)-methyl]-piperidine
2[(2-methoxyphenyl)-pyrrolidin-1-yl-methyl]-1-phenyl-1H-pyrrole
4-{2-[(2-methoxyphenyl)-piperidin-1-yl-methyl]-pyrrol-1-ylmethyl}-pyridine
1(4-fluorophenyl)-2-[(2-methoxyphenyl)-pyrrolidin-1-yl-methyl]-1H-pyrrole
[(1-ethyl-1H-pyrrol-2-yl)-(2-methoxyphenyl)-methyl]-dimethylamine
3-{2-[dimethylamino-(2-methoxyphenyl)-methyl]-pyrrol-1-yl}-propionitrile
dimethyl-[phenyl-(1-phenyl-1H-pyrrol-2-yl)-methyl]-amine
2-[2-(dimethylaminophenylmethyl)-pyrrol-1-yl]-phenylamine
[(1-benzyl-1H-pyrrol-2-yl)-phenylmethyl]-dimethylamine
2-[2-(dimethylaminophenylmethyl)-pyrrol-1-yl]-thiobenzamide
[(1-tert-butyl-1H-pyrrol-2-yl)-phenylmethyl]-dimethylamine
2-[2-(pyrrolidin-1-yl-o-tolylmethyl)-pyrrol-1-yl]-phenylamine
1-methyl-2-(phenylpyrrolidin-1-yl-methyl)-1H-pyrrole
dimethyl-[(1-methyl-1H-pyrrol-2-yl)-phenylmethyl]-amine
2-[2-(piperidin-1-yl-o-tolylmethyl)-pyrrol-1-yl]-thiobenzamide
2-[2-(dimethylamino-o-tolylmethyl)-pyrrol-1-yl]-thiobenzamide
2-[2-(phenylpyrrolidin-1-yl-methyl)-pyrrol-1-yl]-thiobenzamide
2-{2-[(2-methoxyphenyl)-pyrrolidin-1-yl-methyl]-pyrrol-1-yl}-thiobenzamide
2-{2-[(3,4-dimethoxyphenyl)-morpholin-4-yl-methyl]-pyrrol-1-yl}-thiobenzamide
3-{2-[(2-fluoro-phenyl)-piperidin-1-yl-methyl]-pyrrol-1-yl}-propionitrile
2-[(4-bromo-phenyl)-pyrrolidin-1-yl-methyl]-1-phenyl-1H-pyrrole
2-[2-(piperidin-1-yl-m-tolyl-methyl)-pyrrol-1-yl]-phenylamine
2-{2-[(4-bromo-2-fluoro-phenyl)-pyrrolidin-1-yl-methyl]-pyrrol-1-ylmethyl}-pyridine
2-{2-[(3-phenoxy-phenyl)-piperidin-1-yl-methyl]-pyrrol-1-ylmethyl}-pyridine
2-{2-[(3-phenoxy-phenyl)-piperidin-1-yl-methyl]-pyrrol-1-yl}-thiobenzamide
1-[[1-(2-chloro-ethyl)-1H-pyrrol-2-yl]-(4-fluoro-phenyl)-methyl]-piperidine
2-{2-[(3-phenoxy-phenyl)-piperidin-1-yl-methyl]-pyrrol-1-yl}-ethanol
3-[2-(piperidin-1-yl-m-tolyl-methyl)-pyrrol-1-yl]-propan-1-ol
3-{2-[(4-fluoro-phenyl)-piperidin-1-yl-methyl]-pyrrol-1-yl}-propan-1-ol
1-[(4-fluoro-phenyl)-(1-methyl-1H-pyrrol-2-yl)-methyl]-piperidine
1-[(1-methyl-1H-pyrrol-2-yl)-(4-trifluoromethyl-phenyl)-methyl]-piperidine
2-{2-[(2-chloro-6-fluoro-phenyl)-pyrrolidin-1-yl-methyl]-pyrrol-1-yl}-phenylamine
2-{2-[(3-bromo-phenyl)-pyrrolidin-1-yl-methyl]-pyrrol-1-ylmethyl}-pyridine
2-{2-[(3-bromo-4-fluoro-phenyl)-pyrrolidin-1-yl-methyl]-pyrrol-1-ylmethyl}-pyridine
2-{2-[(2-chloro-6-fluoro-phenyl)-pyrrolidin-1-yl-methyl]-pyrrol-1-ylmethyl}-pyridine
4-[(1-pyridin-2-ylmethyl-1H-pyrrol-2-yl)-pyrrolidin-1-ylmethyl]-benzonitrile
2-[(3-bromo-4-fluoro-phenyl)-pyrrolidin-1-yl-methyl]-1-(4-fluoro-phenyl)-1H-pyrrole
2-{2-[(5-bromo-2-fluoro-phenyl)-pyrrolidin-1-yl-methyl]-pyrrol-1-yl}-benzoic acid 2-{2-[(5-bromo-2-fluoro-phenyl)-pyrrolidin-1-yl-methyl]-pyrrol-1-yl}-thiobenzamide
1-tert-butyl-2-[(4-tert-butyl-phenyl)-pyrrolidin-1-yl-methyl]-1H-pyrrole.

The invention also provides processes for the preparation of substituted pyrrole Mannich bases of the general formula I, which are characterized in that
aromatic aldehyde compounds of the general formula II

wherein $R^4$ has the meaning according to the general formula I, are reacted in solution, preferably in an organic solvent, particularly preferably in toluene, in the presence of a base, preferably potassium carbonate or boric acid anhydride, at a temperature of preferably −10° C. to +110° C., with secondary amines of the general formula III

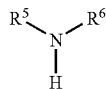

in which $R^5$ and $R^6$ have the meaning according to the general formula I,
to give aminal compounds of the general formula IV

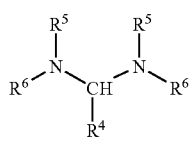

and these aminal compounds of the general formula IV are reacted, without further purification, with acid chlorides, preferably with acetyl chloride, in an absolute solvent, preferably in diethyl ether, to give iminium salts of the general formula V

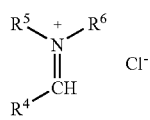

and these iminium salts of the general formula V are reacted, without further purification and in solution, preferably in acetonitrile, with pyrrole and/or substituted pyrrole compounds of the general formula VI

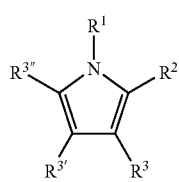

wherein $R^2$=H and the radicals $R^1$, $R^3$, $R^{3'}$, $R^{3''}$ and $R^7$ to $R^{15}$ have the meaning according to the general formula I, to give the pyrrole Mannich bases of the general formula I according to the invention, and the pyrrole Mannich bases of the general formula I obtained in this way are purified by washing, preferably by washing with acetone, and are isolated by conventional methods.

The synthesis of the substituted pyrrole Mannich bases according to the invention is preferably carried out on an automatic unit from Zymark according to FIG. 1 and FIG. 2 as described below.

The compounds of the general formula I can be converted into their salts in a manner known per se to the expert with physiologically tolerated acids, preferably with hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formation is preferably carried out in a solvent, particularly preferably in diethyl ether, diisopropyl ether, acetic acid alkyl esters, acetone and/or 2-butanone. The salt formation is very particularly preferably carried out with trimethylchlorosilane in methyl ethyl ketone.

The substituted pyrrole Mannich bases of the general formula I according to the invention are toxicologically acceptable and are therefore suitable pharmaceutical active compounds.

The invention therefore also provides medicaments which comprise, as the active compound, at least one substituted pyrrole Mannich base of the general formula I and optionally further active compounds and/or auxiliary substances. The medicament can preferably also comprise as the active compound a mixture of enantiomers of at least one substituted pyrrole Mannich base of the general formula I, the mixture preferably not comprising equimolar amounts of the enantiomers. The relative proportion of one of the enantiomers is particularly preferably 5 to 45 mol %, very particularly preferably 10 to 40 mol %, based on the mixture of the enantiomers.

The medicaments are preferably employed for treatment of/combating pain, in particular chronic pain, and/or inflammatory reactions and/or allergic reactions and/or drug abuse and/or alcohol abuse and/or diarrhoea and/or gastritis and/or ulcers and/or cardiovascular diseases and/or urinary incontinence and/or depression and/or states of shock and/or migraines and/or narcolepsy and/or excess weight and/or asthma and/or glaucoma and/or hyperkinetic syndrome and/or lack of drive and/or bulimia and/or anorexia and/or catalepsy and/or for anxiolysis and/or for increasing vigilance and/or for increasing libido.

The present invention also provides the use of at least one substituted pyrrole Mannich base of the general formula I according to the invention for the preparation of a medicament for treatment of/combating pain, in particular chronic pain, and/or inflammatory reactions and/or allergic reactions and/or drug abuse and/or alcohol abuse and/or diarrhoea and/or gastritis and/or ulcers and/or cardiovascular diseases and/or urinary incontinence and/or depression and/or states of shock and/or migraines and/or narcolepsy and/or excess weight and/or asthma and/or glaucoma and/or hyperkinetic syndrome and/or lack of drive and/or bulimia and/or anorexia and/or catalepsy and/or for anxiolysis and/or for increasing vigilance and/or for increasing libido.

In addition to at least one substituted pyrrole Mannich base of the general formula I, carrier materials, fillers, solvents, diluents, dyestuffs and/or binders are employed for formulating appropriate pharmaceutical formulations. The choice of auxiliary substances depends on whether the medicament is to be administered orally, intravenously, intraperitoneally, intradermally, intramuscularly, intranasally, buccally or locally, for example on infections of the skin, the mucous membranes and the eyes. The formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration.

The pyrrole Mannich bases of the general formula I according to the invention in a depot in dissolved form or in a patch, optionally with the addition of agents which promote penetration through the skin, are suitable formulations for percutaneous administration. The compounds of the general formula I according to the invention can be released from oral or percutaneous formulation forms in a delayed manner.

The amount of active compound to be administered to the patient varies according to the weight of the patient, the mode of administration, the indication and the severity of the disease.

Pharmacological Studies:

1.) In vitro Tests

Wide-ranging testing of the pyrrole Mannich bases according to the invention for their activity was carried out by the conventional high throughput screening methods, such as are described in John P. Devlin, High Throughput Screening, 1997, Marcel Dekker Inc. They are introduced here as a reference and are therefore part of the disclosure.

The action of the pyrrole Mannich bases according to the invention is determined in particular by the affinity for the N-methyl-D-aspartate (NMDA) receptor family, for α-adrenergic receptors and opioid receptors.

The investigations of the inhibition of serotonin re-uptake (5-HT uptake inhibition) were carried out by the methods such as are described in M. Ch. Frink, H.-H.-Hennies, W. Englberger, M. Haurand and B. Wilffert, Arzneim.-Forsch./ Drug. Res. 46 (III), 11, 1996, pages 1029–1036. They are introduced herewith as reference and thus form part of the disclosure.

To carry out these investigations, synaptosomes were freshly isolated from rat brain areas. In each case the so-called "P2" fraction was used, which was prepared according to the instructions in E. G. Gray and V. P. Whittaker, J. Anat. 76, pages 79–88, 1962. This literature is introduced herewith as reference and thus forms part of the disclosure. For determination of the 5-HT uptake, these vesicular particles were isolated from the pons and medulla oblongata region of the male rat brain.

The following characteristic data were determined for the 5-HT transporter:

5-HT uptake: $K_m = 0.084 \pm 0.011$ μM $V_{max}$: 38.13±4.52 pmol/min/mg protein.

The results of the investigations are in each case stated as means from 2 parallel experiments.

2.) Analgesia Test in the Writhing Test in Mice

The in-depth investigation for analgesic activity was carried out in the phenylquinone-induced writhing in mice (modified by I. C. Hendershot, J. Forsaith, J. Pharmacol. Exp. Ther. 125, 237–240 (1959)). Male NMRI mice weighing 25–30 g were used for this. Groups of 10 animals per substance dose received 0.3 ml/mouse of a 0.02% aqueous solution of phenylquinone (phenylbenzoquinone, Sigma, Deisenhofen; preparation of the solution with the addition of 5% ethanol and storage in a water bath at 45° C.) administered intraperitoneally 10 minutes after intravenous administration of the test substances. The animals were placed individually in observation cages. The number of pain-induced stretching movements (so-called writhing reactions=straightening of the body with stretching of the hind extremities) were counted by means of a push-button counter for 5–20 minutes after the administration of phenylquinone. Animals which received only physiological saline solution were also run as a control.

The substances were tested in the standard dose of 10 mg/kg. The inhibition of the writhing reactions by a substance was calculated according to the following equation:

$$\% \text{ inhibition} = 100 - \left[ \frac{\text{writhing reaction of treated animals}}{\text{writhing reaction of control}} \times 100 \right]$$

The following examples serve to illustrate the invention, but do not limit the general inventive idea.

EXAMPLES

General Synthesis Instructions for the Preparation of Aminal Compounds of the General Formula IV General Synthesis Instructions 1:

1.0 equivalent of the particular aromatic aldehyde compound of the general formula II was slowly added dropwise, while stirring at 20° C., to 2.7 equivalents of a 40% solution of the particular secondary amine with the general formula III. The solution was then subsequently stirred at a temperature of 80° C. for a further 30 minutes and then cooled to room temperature, and 0.57 equivalent of potassium carbonate was added. Two phases formed here and were separated from one another, the aqueous phase being extracted three times with 100 ml ethyl acetate each time. The combined organic phases were dried over potassium carbonate and freed from the solvent. The aminal compounds of the general formula IV obtained in this way were then employed in the subsequent reactions without further purification.

General Synthesis Instructions 2:

1.6 equivalents of boric acid anhydride were added to a solution of 1.0 equivalent of the particular aromatic aldehyde compound of the general formula II in 80 ml absolute toluene. A solution of 2.4 equivalents of a secondary amine of the general formula III in 85 ml absolute toluene was then added with vigorous stirring. Starting of the reaction could be seen by a significant increase in temperature. The reaction solution was then subsequently stirred at a temperature of 45 to 50° C. for a further two hours. After cooling to room temperature the excess boric acid anhydride was separated off and the filtrate was freed from the solvent. The aminal compounds of the general formula IV obtained in this way were employed in the subsequent reactions without further purification.

General Synthesis Instructions for the Synthesis of Iminium Salts of the General Formula V General Synthesis Instructions 3:

A solution of 1.0 equivalent of acetyl chloride in absolute diethyl ether was slowly added dropwise, while stirring, to 1.0 equivalent of an ice-cooled solution or suspension of the aminal compound of the general formula IV prepared in accordance with general synthesis instructions 1 or 2. The reaction mixture was then subsequently stirred overnight at approx. 20° C. A precipitate was formed here, and was filtered off with suction under nitrogen and then dried under an oil pump vacuum. The iminium salts of the general formula V obtained in this way were employed in the subsequent reactions without further purification.

Figure 2:
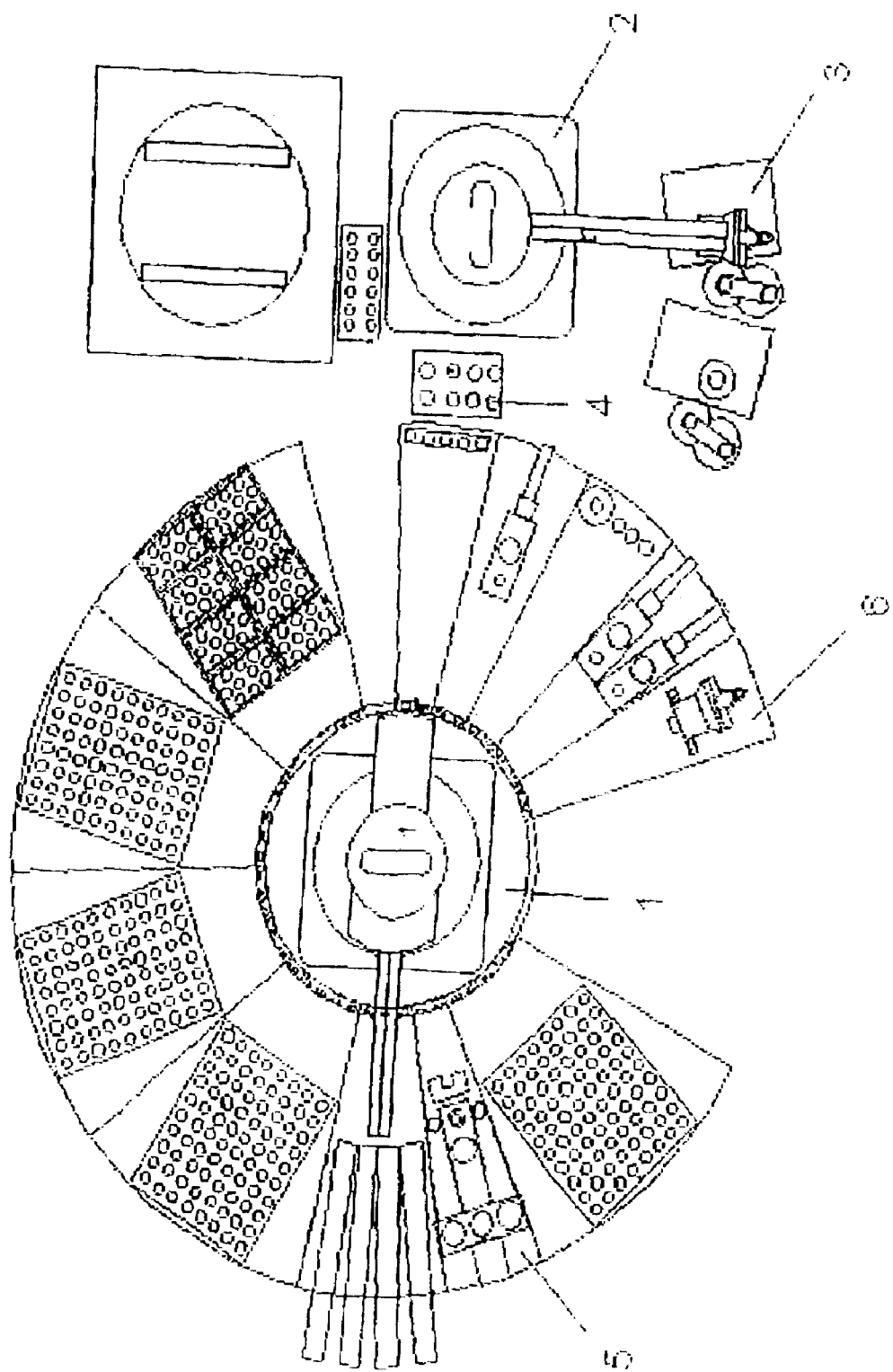

General Synthesis Instructions for the Synthesis of Pyrrole Mannich Bases of the General Formula I General Synthesis Instructions 4:

The synthesis of the pyrrole Mannich bases according to the invention was carried out on an automatic unit from Zymark according to FIG. 1 and FIG. 2:

FIG. 1 here comprises a capper station (no. 1) for closing the reaction tubes, a robot 1 (no. 2) and a robot 2 (no. 3), robot 1 moving the reaction tubes and robot 2 pipetting the reagents into the reaction tubes, a temperature-controllable reactor block (no. 4), stirrer blocks (no. 5) and a filtration station (no. 6), in which the reaction solution is filtered.

FIG. 2 also comprises a robot 1 (no. 1) and a robot 2 (no. 2), the two robots bringing the vessels with the reaction products to the various stations at which the synthesis products from the automatic synthesis unit according to FIG. 1 are worked up. Acetone is added to the synthesis products here on a vortexer (no. 3), the components are mixed thoroughly in a spin reactor (no. 4) and the acetone is then decanted off.

For the synthesis, a round-bottomed tube of glass (diameter 16 mm, length 125 mm) with a screw-thread was provided manually with a stirrer and closed with a screw-cap with a septum on the capper station (no. 1) according to FIG. 1. The tube was placed by robot 1 (no. 2) in the reactor block, which was temperature-controlled at 0° C. Robot 2 (no. 3) pipetted in the following reagents in succession:

1.) 1 ml of a 0.1 M solution of pyrrole or a substituted pyrrole compound of the general formula VI in acetonitrile
2.) 1.2 ml of a 0.1 M solution of an iminium salt of the general formula V in acetonitrile The iminium salts were prepared beforehand as described in the following examples. Thereafter, the reaction mixture was stirred at 18° C. in one of the stirrer blocks (no. 5) for 960 min. The reaction solution was then filtered at the filtration station (no. 6).

The solvent was first removed in a vacuum centrifuge. The rack with the tubes was then placed manually on a vortexer (no. 3) according to FIG. 2. 2 ml acetone were added to the reaction mixture there. The components were mixed thoroughly in the spin reactor (no. 4) for 10 minutes and finally the acetone was decanted off. This process was carried out a further three times and finally the solvent was removed in a vacuum centrifuge.

Example 1

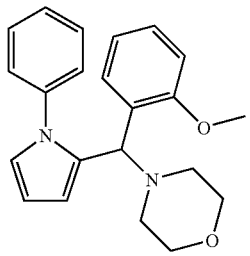

4-[(2-Methoxyphenyl)-(1-phenyl-1H-pyrrol-2-yl)-methyl]-morpholine

1st Stage 4-(2-Methoxy-benzylidene)-morpholin-4-ium chloride

The reaction of 18.8 ml (0.216 mol) morpholine and 12.4 g (0.09 mol) 2-methoxybenzaldehyde in accordance with general synthesis instructions 2 and subsequent reaction with 5.3 ml (0.110 mol) acetyl chloride in accordance with general synthesis instructions 3 gave 7.61 g (corresponding to 38% of the yield calculated by theory) 4-(2-methoxy-benzylidene)-morpholin-4-ium chloride.

2nd Stage

4-[(2-Methoxyphenyl)-(1-phenyl-1H-pyrrol-2-yl)-methyl]-morpholine

The preparation was carried out in accordance with general synthesis instructions 4 from 1-phenyl-1H-pyrrole and 4-(2-methoxy-benzylidene)-morpholin-4-ium chloride.

For characterization, an ESI-MS was recorded: MS-(EI) m/z: 262.4 (M*).

Example 2

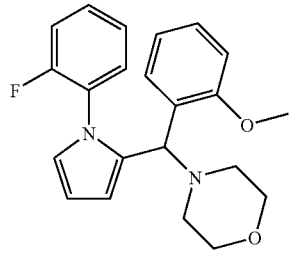

4-[[1-(2-Fluorophenyl)-1H-pyrrol-2-yl]-(2-methoxyphenyl)-methyl]-morpholine

The preparation was carried out in accordance with general synthesis instructions 4 from 1-(2-fluoro-phenyl)-1H-pyrrole and 4-(2-methoxy-benzylidene)-morpholin-4-ium chloride, which had been prepared in accordance with example 1.

For characterization, an ESI-MS was recorded: MS-(EI) m/z: 280.3 (M*).

Example 3

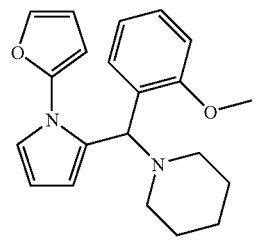

1-[(1-Furan-2-yl-1H-pyrrol-2-yl)-(2-methoxyphenyl)-methyl]-piperidine

1st Stage 1-(2-Methoxy-benzylidene)-piperidinium chloride

The reaction of 18.4 g (0.216 mol) piperidine and 25.9 g (0.090 mol) 2-methoxybenzaldehyde in accordance with general synthesis instructions 2 and subsequent reaction with 5.3 ml (0.11 mol) acetyl chloride in accordance with general synthesis instructions 3 gave 13.4 g (corresponding to 62% of the yield calculated by theory) 1-(2-methoxy-benzylidene)-piperidinium chloride.

2nd Stage

1-[(1-Furan-2-yl-1H-pyrrol-2-yl)-(2-methoxyphenyl)-methyl]-piperidine

The preparation was carried out in accordance with general synthesis instructions 4 from 1-furan-2-yl-1H-pyrrole and 1-(2-methoxy-benzylidene)-piperidinium chloride.

For characterization, an ESI-MS was recorded: MS (EI) m/z: 351.1, 266.3 (M*).

Example 4

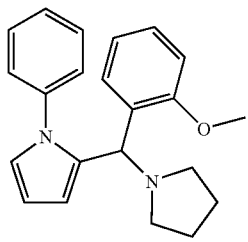

2-[(2-Methoxyphenyl)-pyrrolidin-1-yl-methyl]-1-phenyl-1H-pyrrole

1st Stage 1-(2-Methoxy-benzylidene)-pyrrolidinium chloride

The reaction of 6.9 ml (0.084 mol) pyrrolidine and 4.8 g (0.035 mol) 2-methoxybenzaldehyde in accordance with general synthesis instructions 2 and subsequent reaction with 2.1 ml (0.035 mol) acetyl chloride in accordance with general synthesis instructions 3 gave 6.2 g (corresponding to 78% of the yield calculated by theory) 1-(2-methoxy-benzylidene)-pyrrolidinium chloride.

2nd Stage

2-[(2-Methoxyphenyl)-pyrrolidin-1-yl-methyl]-1-phenyl-1H-pyrrole

The preparation was carried out in accordance with general synthesis instructions 4 from 1-phenyl-1H-pyrrole and 1-(2-methoxy-benzylidene)pyrrolidinium chloride.

For characterization, an ESI-MS was recorded: MS (EI) m/z: 333.0, 262.4 (M*).

Example 5

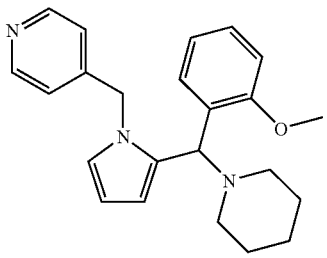

4-{2-[(2-Methoxyphenyl)-piperidin-1-yl-methyl]-pyrrol-1-yl-methyl}-pyridine

The preparation was carried out in accordance with general synthesis instructions 4 from 4-pyrrol-1-yl-methyl-pyridine and 1-(2-methoxy-benzylidene)-piperidinium chloride, which had been prepared in accordance with example 3.

For characterization, an ESI-MS was recorded: MS-(EI) m/z: 362.1, 277.4 (M*).

Example 6

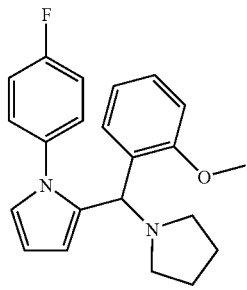

1-(4-Fluorophenyl)-2-[(2-methoxyphenyl)-pyrrolidin-1-yl-methyl]-1H-pyrrole

The preparation was carried out in accordance with general synthesis instructions 4 from 1-(4-fluoro-phenyl)-1H-pyrrole and 1-(2-methoxy-benzylidene)-pyrrolidinium chloride, which had been prepared in accordance with example 4.

For characterization, an ESI-MS was recorded: MS-(EI) m/z: 348.5, 280.4 (M*).

Example 7

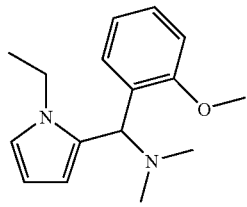

[(1-Ethyl-1H-pyrrol-2-yl)-(2-methoxyphenyl)-methyl]-dimethylamine

1st Stage (2-Methoxy-benzylidene)-dimethyl-ammonium chloride

The reaction of 17.0 ml (0.135 mol) dimethylamine solution and 6.8 g (0.050 mol) 2-methoxybenzaldehyde in accordance with general synthesis instructions 1 and subsequent reaction with 3.0 ml (0.050 mol) acetyl chloride in accordance with general synthesis instructions 3 gave 4.8 g (corresponding to 48% of the yield calculated by theory) 2-methoxy-benzylidene-dimethyl-ammonium chloride.

2nd Stage

[(1-Ethyl-1H-pyrrol-2-yl)-(2-methoxyphenyl)-methyl]-dimethylamine

The preparation was carried out in accordance with general synthesis instructions 4 from 1-ethyl-1H-pyrrole and (2-methoxy-benzylidene)-dimethyl-ammonium chloride.

For characterization, an ESI-MS was recorded: MS (EI) m/z: 214.5 (M*).

Example 8

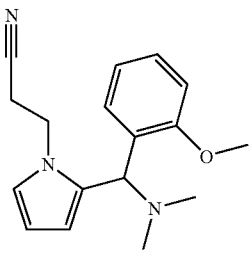

3-{2-[Dimethylamino-(2-methoxyphenyl)-methyl]-pyrrol-1-yl}-propionitrile

The preparation was carried out in accordance with general synthesis instructions 4 from 3-pyrrol-1-yl-propionitrile and (2-methoxy-benzylidene)-dimethyl-ammonium chloride, which had been prepared in accordance with example 7.

For characterization, an ESI-MS was recorded: MS-(EI) m/z: 209.4 (M*).

Example 9

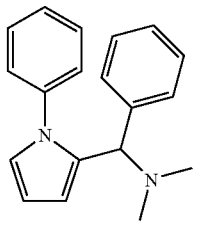

Dimethyl-[phenyl-(1-phenyl-1H-pyrrol-2-yl)-methyl]-amine

1st Stage

Benzylidene-dimethyl-ammonium chloride

The reaction of 32.0 ml (0.213 mol) dimethylamine solution and 8.0 ml (0.079 mol) benzaldehyde in accordance with general synthesis instructions 1 and subsequent reaction with 4.7 ml (0.079 mol) acetyl chloride in accordance with general synthesis instructions 3 gave 9.5 g (corresponding to 70.7% of the yield calculated by theory) benzylidene-dimethyl-ammonium chloride.

2nd Stage

Dimethyl-[phenyl-(1-phenyl-1H-pyrrol-2-yl)-methyl]-amine

The preparation was carried out in accordance with general synthesis instructions 4 from 1-phenyl-1H-pyrrole and benzylidene-dimethyl-ammonium chloride.

For characterization, an ESI-MS was recorded: MS (EI) m/z: 232.4 (M*).

Example 10

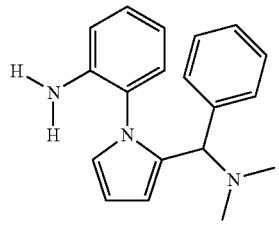

2-[2-(Dimethylaminophenylmethyl)-pyrrol-1-yl]-phenylamine

The preparation was carried out in accordance with general synthesis instructions 4 from 2-pyrrol-1-yl-phenylamine and benzylidene-dimethyl-ammonium chloride, which had been prepared in accordance with example 9.

For characterization, an ESI-MS was recorded: MS-(EI) m/z: 245.5 (M*).

Example 11

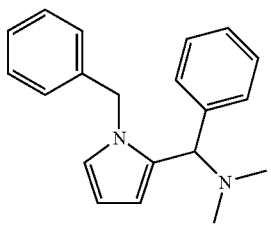

[(1-Benzyl-1H-pyrrol-2-yl)-phenylmethyl]-dimethylamine

The preparation was carried out in accordance with general synthesis instructions 4 from 1-benzyl-1H-pyrrole and benzylidene-dimethyl-ammonium chloride, which had been prepared in accordance with example 9.

For characterization, an ESI-MS was recorded: MS-(EI) m/z: 247.4, 204.0 (M*).

Example 12

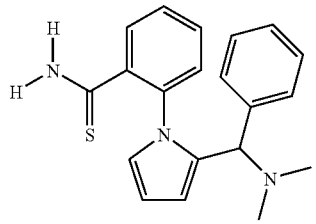

2-[2-(Dimethylaminophenylmethyl)-pyrrol-1-yl]-thiobenzamide

The preparation was carried out in accordance with general synthesis instructions 4 from 2-pyrrol-1-yl-thiobenzamide and benzylidene-dimethyl-ammonium chloride, which had been prepared in accordance with example 9.

For characterization, an ESI-MS was recorded: MS-(EI) m/z: 335.9 (M*).

Example 13

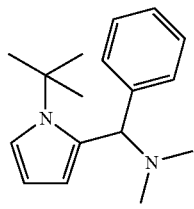

[(1-tert-Butyl-1H-pyrrol-2-yl)-phenylmethyl]-dimethylamine

The preparation was carried out in accordance with general synthesis instructions 4 from 1-tert-butyl-1H-pyrrole and benzylidene-dimethyl-ammonium chloride, which had been prepared in accordance with example 9.

For characterization, an ESI-MS was recorded: MS-(EI) m/z: 296.3 (M*).

Example 14

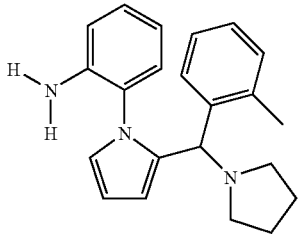

2-[2-(Pyrrolidin-1-yl-o-tolylmethyl)-pyrrol-1-yl]-phenylamine

1st Stage 1-(2-Methyl-benzylidene)-pyrrolidinium chloride

The reaction of 8.2 ml (0.100 mol) pyrrolidine and 7.0 g (0.050 mol) 2-methylbenzaldehyde in accordance with general synthesis instructions 2 and subsequent reaction with 3.9 g (0.050 mol) acetyl chloride in accordance with general synthesis instructions 3 gave 6.6 g (corresponding to 63% of the yield calculated by theory) 1-(2-methyl-benzylidene)-pyrrolidinium chloride.

2nd Stage

2-[2-(Pyrrolidin-1-yl-o-tolylmethyl)-pyrrol-1-yl]-phenylamine

The preparation was carried out in accordance with general synthesis instructions 4 from 2-pyrrol-1-yl-phenylamine and 1-(2-methyl-benzylidene)-pyrrolidinium chloride.

For characterization, an ESI-MS was recorded: MS (EI) m/z: 261.4 (M*).

Example 15

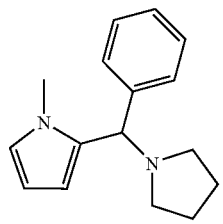

1-Methyl-2-(phenylpyrrolidin-1-yl-methyl)-1H-pyrrole

1st Stage

1-Benzylidene-pyrrolidinium chloride

The reaction of 16.4 ml (0.200 mol) pyrrolidine and 10.1 ml (0.100 mol) benzaldehyde in accordance with general synthesis instructions 2 and subsequent reaction with 6.0 ml (0.100 mol) acetyl chloride in accordance with general synthesis instructions 3 gave 14.1 g (corresponding to 72% of the yield calculated by theory) 1-benzylidene-pyrrolidinium chloride.

2nd Stage

1-Methyl-2-(phenylpyrrolidin-1-yl-methyl)-1H-pyrrole

The preparation was carried out in accordance with general synthesis instructions 4 from 1-methyl-1H-pyrrole and 1-benzylidene-pyrrolidinium chloride.

For characterization, an ESI-MS was recorded: MS (EI) m/z: 240.9 (M*).

Example 16

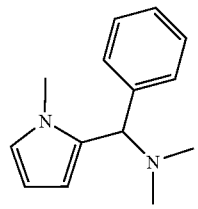

Dimethyl-[(1-methyl-1H-pyrrol-2-yl)-phenylmethyl]-amine

The preparation was carried out in accordance with general synthesis instructions 4 from 1-methyl-1H-pyrrole and benzylidene-dimethyl-ammonium chloride, which had been prepared in accordance with example 9.

For characterization, an ESI-MS was recorded: MS-(EI) m/z: 214.3 (M*).

Example 17

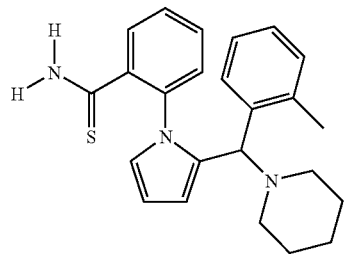

2-[2-(Piperidin-1-yl-o-tolylmethyl)-pyrrol-1-yl]-thiobenzamide

1st Stage
1-(2-Methyl-benzylidene)-piperidinium chloride

The reaction of 9.5 ml (0.096 mol) piperidine and 4.7 ml (0.040 mol) 2-methylbenzaldehyde in accordance with general synthesis instructions 2 and subsequent reaction with 2.4 ml (0.040 mol) acetyl chloride in accordance with general synthesis instructions 3 gave 5.8 g (corresponding to 65% of the yield calculated by theory) 1-(2-methyl-benzylidene)-piperidinium chloride.

2nd Stage
2-[2-(Piperidin-1-yl-o-tolylmethyl)-pyrrol-1-yl]-thiobenzamide

The preparation was carried out in accordance with general synthesis instructions 4 from 2-pyrrol-1-yl-thiobenzamide and 1-(2-methyl-benzylidene)-piperidinium chloride.

For characterization, an ESI-MS was recorded: MS (EI) m/z: 305.4, 275.5 (M*).

Example 18

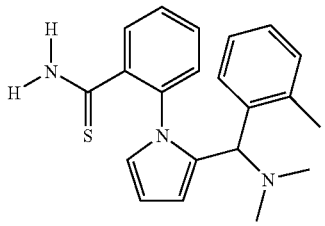

2-[2-(Dimethylamino-o-tolylmethyl)-pyrrol-1-yl]-thiobenzamide

1st Stage
Dimethyl-(2-methyl-benzylidene)-ammonium chloride

The reaction of 14.0 ml (0.108 mol) dimethylamine solution and 4.6 ml (0.040 mol) 2-methylbenzaldehyde in accordance with general synthesis instructions 1 and subsequent reaction with 2.4 ml (0.040 mol) acetyl chloride in accordance with general synthesis instructions 3 gave 5.3 g (corresponding to 73% of the yield calculated by theory) dimethyl-(2-methyl-benzylidene)-ammonium chloride.

2nd Stage
2-[2-(Dimethylamino-o-tolylmethyl)-pyrrol-1-yl]-thiobenzamide

The preparation was carried out in accordance with general synthesis instructions 4 from 2-pyrrol-1-yl-thiobenzamide and dimethyl-(2-methyl-benzylidene)-ammonium chloride.

For characterization, an ESI-MS was recorded: MS (EI) m/z: 351.1, 305.4 (M*).

Example 19

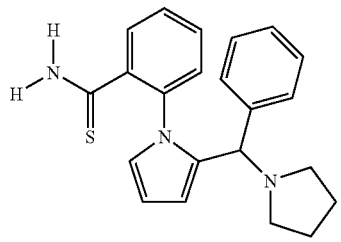

2-[2-(Phenylpyrrolidin-1-yl-methyl)-pyrrol-1-yl]-thiobenzamide

The preparation was carried out in accordance with general synthesis instructions 4 from 2-pyrrol-1-yl-thiobenzamide and 1-benzylidene-pyrrolidinium chloride, which had been prepared in accordance with example 15.

For characterization, an ESI-MS was recorded: MS (EI) m/z: 361.9, 291.2 (M*).

Example 20

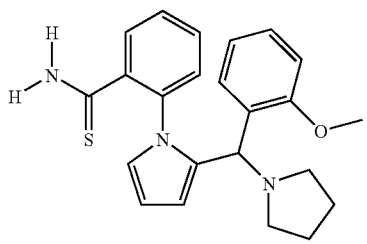

2-{2-[(2-Methoxyphenyl)-pyrrolidin-1-yl-methyl]-pyrrol-1-yl}-thiobenzamide

The preparation was carried out in accordance with general synthesis instructions 4 from 2-pyrrol-1-yl-thiobenzamide and 1-(2-methoxy-benzylidene)-pyrrolidinium chloride, which had been prepared in accordance with example 4.

For characterization, an ESI-MS was recorded: MS (EI) m/z: 392, 321.3 (M*).

Example 21

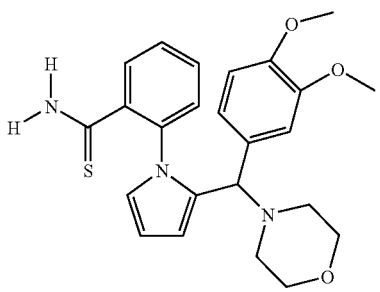

2-{2-[(3,4-Dimethoxyphenyl)-morpholin-4-yl-methyl]-pyrrol-1-yl}-thiobenzamide

1st Stage
4-(2,3-Dimethoxy-benzylidene)-morpholin-4-ium chloride

The reaction of 7.3 ml (0.084 mol) morpholine and 5.8 g (0.035 mol) 2,3-dimethoxybenzaldehyde in accordance with general synthesis instructions 2 and subsequent reaction with 2.1 ml (0.035 mol) acetyl chloride in accordance with general synthesis instructions 3 gave 5.6 g (corresponding to 59% of the yield calculated by theory) 4-(2,3-dimethoxy-benzylidene)-morpholin-4-ium chloride 2nd Stage
2-{2-[(3,4-Dimethoxyphenyl)-morpholin-4-yl-methyl]-pyrrol-1-yl}-thiobenzamide The preparation was carried out in accordance with general synthesis instructions 4 from 2-pyrrol-1-yl-thiobenzamide and 4-(2,3-dimethoxy-benzylidene)-morpholin-4-ium chloride.

For characterization, an ESI-MS was recorded: MS (EI) m/z: 437.53, 407.8, 351.3 (M*).

Example 22

3-{2-[(2-Fluoro-phenyl)-piperidin-1-yl-methyl]-pyrrol-1-yl}-propionitrile

The preparation was carried out in accordance with general synthesis instructions 4 from 3-pyrrol-1-yl-propionitrile and 1-(2-fluoro-benzylidene)-piperidinium chloride, which had been prepared in accordance with example 3 from 2-fluorobenzaldehyde and piperidine.

Example 23

2-[(4-Bromo-phenyl)-pyrrolidin-1-yl-methyl]-1-phenyl-1H-pyrrole

The preparation was carried out in accordance with general synthesis instructions 4 from 1-phenyl-1H-pyrrole and 1-(4-bromo-benzylidene)-pyrrolidinium chloride, which had been prepared in accordance with example 4 from 4-bromobenzaldehyde and pyrrolidine.

Example 24

2-[2-(Piperidin-1-yl-m-tolyl-methyl)-pyrrol-1-yl]-phenylamine

The preparation was carried out in accordance with general synthesis instructions 4 from 2-pyrrol-1-yl-phenylamine and 1-(3-methyl-benzylidene)-piperidinium chloride, which had been prepared in accordance with example 3 from 3-methylbenzaldehyde and piperidine.

Example 25

2-{2-[(4-Bromo-2-fluoro-phenyl)-pyrrolidin-1-yl-methyl]-pyrrol-1-ylmethyl}-pyridine The preparation was carried out in accordance with general synthesis instructions 4 from 4-pyrrol-1-yl-methyl-pyridine and 1-(4-bromo-2-fluoro-benzylidene)-pyrrolidinium chloride, which had been prepared in accordance with example 4 from 4-bromo-2-fluorobenzaldehyde and pyrrolidine.

Example 26

2-{2-[(3-Phenoxy-phenyl)-piperidin-1-yl-methyl]-pyrrol-1-ylmethyl}-pyridine

The preparation was carried out in accordance with general synthesis instructions 4 from 4-pyrrol-1-yl-methyl-pyridine and 1-(3-phenoxy-benzylidene)-piperidinium chloride, which had been prepared in accordance with example 3 from 3-phenoxybenzaldehyde and piperidine.

Example 27

2-{2-[(3-Phenoxy-phenyl)-piperidin-1-yl-methyl]-pyrrol-1-yl}-thiobenzamide

The preparation was carried out in accordance with general synthesis instructions 4 from 2-pyrrol-1-yl-thiobenzamide and 1-(3-phenoxy-benzylidene)-piperidinium chloride, which had been prepared in accordance with example 3 from 3-phenoxybenzaldehyde and piperidine.

Example 28

1-[[1-(2-Chloro-ethyl)-1H-pyrrol-2-yl]-(4-fluoro-phenyl)-methyl]-piperidine

The preparation was carried out in accordance with general synthesis instructions 4 from 2-pyrrol-1-yl-chloroethane and 1-(4-fluoro-benzylidene)-piperidinium chloride, which had been prepared in accordance with example 3 from 4-fluorobenzaldehyde and piperidine.

Example 29

2-{2-[(3-Phenoxy-phenyl)-piperidin-1-yl-methyl]-pyrrol-1-yl}-ethanol

The preparation was carried out in accordance with general synthesis instructions 4 from 2-pyrrol-1-yl-ethanol and 1-(3-phenoxy-benzylidene)-piperidinium chloride, which had been prepared in accordance with example 3 from 3-phenoxybenzaldehyde and piperidine.

Example 30

3-[2-(Piperidin-1-yl-m-tolyl-methyl)-pyrrol-1-yl]-propan-1-ol

The preparation was carried out in accordance with general synthesis instructions 4 from 3-pyrrol-1-yl-propanol and 1-(3-methyl-benzylidene)-piperidinium chloride, which had been prepared in accordance with example 3 from 3-methylbenzaldehyde and piperidine.

Example 31

3-{2-[(4-Fluoro-phenyl)-piperidin-1-yl-methyl]-pyrrol-1-yl}-propan-1-ol

The preparation was carried out in accordance with general synthesis instructions 4 from 3-pyrrol-1-yl-propanol and 1-(4-fluorobenzylidene)-piperidinium chloride, which had been prepared in accordance with example 3 from 4-fluorobenzaldehyde and piperidine.

Example 32

1-[(4-Fluoro-phenyl)-(1-methyl-1H-pyrrol-2-yl)-methyl]-piperidine

The preparation was carried out in accordance with general synthesis instructions 4 from 1-methyl-1H-pyrrole and 1-(4-fluoro-benzylidene)-piperidinium chloride, which had been prepared in accordance with example 3 from 4-fluorobenzaldehyde and piperidine.

Example 33

1-[(1-Methyl-1H-pyrrol-2-yl)-(4-trifluoromethyl-phenyl)-methyl]-piperidine

The preparation was carried out in accordance with general synthesis instructions 4 from 1-methyl-1H-pyrrole and 1-(4-trifluoromethyl-benzylidene)-piperidinium chloride, which had been prepared in accordance with example 3 from 4-trifluoromethylbenzaldehyde and piperidine.

Example 34

2-{2-[(2-Chloro-6-fluoro-phenyl)-pyrrolidin-1-yl-methyl]-pyrrol-1-yl}-phenylamine The preparation was carried out in accordance with general synthesis instructions 4 from 2-pyrrol-1-yl-phenylamine and 1-(2-chloro-6-fluoro-benzylidene)-pyrrolidinium chloride, which had been prepared in accordance with example 4 from 2-chloro-6-fluorobenzaldehyde and pyrrolidine.

Example 35

2-{2-[(3-Bromo-phenyl)-pyrrolidin-1-yl-methyl]-pyrrol-1-ylmethyl}-pyridine

The preparation was carried out in accordance with general synthesis instructions 4 from 4-pyrrol-1-yl-methyl-pyridine and 1-(3-bromo-benzylidene)-pyrrolidinium chloride, which had been prepared in accordance with example 4 from 3-bromobenzaldehyde and pyrrolidine.

Example 36

2-{2-[(3-Bromo-4-fluoro-phenyl)-pyrrolidin-1-yl-methyl]-pyrrol-1-ylmethyl}-pyridine The preparation was carried out in accordance with general synthesis instructions 4 from 4-pyrrol-1-yl-methyl-pyridine and 1-(3-bromo-4-fluoro-benzylidene)-pyrrolidinium chloride, which had been prepared in accordance with example 4 from 3-bromo-4-fluorobenzaldehyde and pyrrolidine.

Example 37

2-{2-[(2-Chloro-6-fluoro-phenyl)-pyrrolidin-1-yl-methyl]-pyrrol-1-ylmethyl}-pyridine The preparation was carried out in accordance with general synthesis instructions 4 from 4-pyrrol-1-yl-methyl-pyridine and 1-(2-chloro-6-fluoro-benzylidene)-pyrrolidinium chloride, which had been prepared in accordance with example 4 from 2-chloro-6-fluorobenzaldehyde and pyrrolidine.

Example 38

4-[(1-Pyridin-2-ylmethyl-1H-pyrrol-2-yl)-pyrrolidin-1-yl-methyl]-benzonitrile

The preparation was carried out in accordance with general synthesis instructions 4 from 4-pyrrol-1-yl-methyl-pyridine and 1-(4-cyano-benzylidene)-pyrrolidinium chloride, which had been prepared in accordance with example 4 from 4-cyanobenzaldehyde and pyrrolidine.

Example 39

2-[(3-Bromo-4-fluoro-phenyl)-pyrrolidin-1-yl-methyl]-1-(4-fluoro-phenyl)-1H-pyrrole The preparation was carried out in accordance with general synthesis instructions 4 from 1-(4-fluoro-phenyl)-1H-pyrrole and 1-(3-bromo-4-fluoro-benzylidene)-pyrrolidinium chloride, which had been prepared in accordance with example 4 from 3-bromo-4-fluorobenzaldehyde and pyrrolidine.

Example 40

2-{2-[(5-Bromo-2-fluoro-phenyl)-pyrrolidin-1-yl-methyl]-pyrrol-1-yl}-benzoic acid The preparation was carried out in accordance with general synthesis instructions 4 from 1-benzoic acid-1H-pyrrole and 1-(5-bromo-2-fluoro-benzylidene)-pyrrolidinium chloride, which had been prepared in accordance with example 4 from 5-bromo-2-fluorobenzaldehyde and pyrrolidine.

Example 41

2-{2-[(5-Bromo-2-fluoro-phenyl)-pyrrolidin-1-yl-methyl]-pyrrol-1-yl}-thiobenzamide The preparation was carried out in accordance with general synthesis instructions 4 from 2-pyrrol-1-yl-thiobenzamide and 1-(5-bromo-2-fluoro-benzylidene)-pyrrolidinium chloride, which had been prepared in accordance with example 4 from 5-bromo-2-fluorobenzaldehyde and pyrrolidine.

Example 42

1-tert-Butyl-2-[(4-tert-butyl-phenyl)-pyrrolidin-1-yl-methyl]-1H-pyrrole

The preparation was carried out in accordance with general synthesis instructions 4 from 1-tert-butyl-1H-pyrrole and 1-(4-tert-butylbenzylidene)-pyrrolidinium chloride, which had been prepared in accordance with example 4 from 4-tert-butylbenzaldehyde and pyrrolidine.

Pharmacological Studies

1.) In vitro Tests

The pyrrole Mannich bases according to the invention were tested for their activity as described above.

The compounds according to the invention investigated showed an inhibition of serotonin re-uptake.

The results of selected investigations of the inhibitions of serotonin re-uptake are reproduced in the following table 1:

TABLE 1

| Example no. | Inhibition of 5HT uptake in % |
|---|---|
| 22 | 83 |
| 23 | 57 |
| 24 | 59 |
| 25 | 52 |
| 26 | 71 |
| 27 | 44 |
| 28 | 40 |
| 29 | 48 |
| 30 | 43 |
| 31 | 50 |
| 32 | 42 |
| 33 | 55 |
| 34 | 39 |
| 35 | 43 |
| 36 | 63 |
| 37 | 39 |
| 38 | 45 |
| 39 | 37 |
| 40 | 51 |
| 41 | 41 |
| 42 | 53 |

2.) Analgesia Test in the Writhing Test in Mice

The in-depth investigation for analgesic activity was carried out in the phenylquinone-induced writhing in mice as described above.

The compounds according to the invention investigated showed an analgesic action.

The results of selected writhing investigations are summarized in the following table 2.

TABLE 2

Analgesia test in the writhing test in mice

| Example no. | Inhibition of the Writhing reaction in % |
|---|---|
| 15 | 87 |
| 16 | 17 |

What is claimed is:

1. A substituted pyrrole Mannich base of formula I

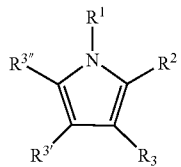

I wherein
$R^1$=H, a $C_{1-10}$-alkyl, an aryl radical, a heteroaryl radical selected from the group consisting of furoyl, thiophene and pyridine radical, which is unsubstituted or at least monosubstituted by F, Cl, Br, $NH_2$, $NO_2$, $NH_2$—(C=S) or COOH, or
an aryl, said heteroaryl, CN, Br, Cl or OH radical bonded via a $C_{1-6}$-alkylene group,
$R^2$=CH($R^4$)N($R^5$)($R^6$),
$R^3$, $R^{3'}$, $R^{3''}$ are identical or different and are H, F, Cl, Br, $CF_3$, CN, $NO_2$, $SO_2NH_2$, $NHR^7$, $SR^8$, $OR^9$, $CO(OR^{10})$, $CH_2CO(OR^{11})$, $COR^{15}$, a $C_{1-10}$-alkyl, an aryl radical, or an aryl radical bonded via a $C_{1-6}$-alkylene group,
$R^4$=an unsubstituted phenyl radical or a phenyl radical which is at least monosubstituted by $C_{1-4}$-alkyl, $C_{1-3}$-alkoxy, halogen, $CF_3$, CN, O-phenyl or OH, $R^5$, $R^6$ are identical or different and are a branched or unbranched, saturated or unsaturated, unsubstituted or at least monosubstituted $C_{1-6}$-alkyl radical or an unsubstituted or at least monosubstituted phenyl, benzyl or phenethyl radical,
or $R^5$ and $R^6$ together denote $(CH_2)_n$, where n=an integer from 3 to 6, or $(CH_2)_2O(CH_2)_2$,
$R^7$=H, $COR^{12}$, a $C_{1-10}$-alkyl, an aryl radical, or an aryl bonded via a $C_{1-6}$-alkylene group,
$R^8$=H, a $C_{1-10}$-alkyl, an aryl radical, or an aryl bonded via a $C_{1-6}$-alkylene group,
$R^9$=H, $COR^{13}$, a $C_{1-10}$-alkyl, an aryl radical, or an aryl bonded via a $C_{1-6}$-alkylene group,
$R^{10}$=H, a $C_{1-10}$-alkyl, an aryl radical, or an aryl bonded via a $C_{1-6}$-alkylene group,
$R^{11}$=H, a $C_{1-10}$-alkyl, an aryl radical, or an aryl bonded via a $C_{1-6}$-alkylene group,
$R^{12}$=a $C_{1-10}$-alkyl, an aryl radical, or an aryl bonded via a $C_{1-6}$-alkylene group,
$R^{13}$=a $C_{1-10}$-alkyl, an aryl radical, or an aryl bonded via a $C_{1-6}$-alkylene group,
$R^{14}$=H, a $C_{1-10}$-alkyl, an aryl radical, or an aryl bonded via a $C_{1-6}$-alkylene group,
$R^{15}$=$NHNH_2$, $NHR^{14}$, a $C_{1-10}$-alkyl, an aryl radical, or an aryl bonded via a $C_{1-6}$-alkylene group,
and/or racemates, enantiomers, or diastereomers thereof, and/or corresponding bases and/or corresponding salts of physiologically tolerated acids thereof,
excluding a racemate of a compound of formula I in which the radicals $R^1$, $R^3$, $R^{3'}$ and $R^{3''}$ each=H, the radical $R^2$=CH($R^4$)N($R^5$)($R^6$), the radical $R^4$=a phenyl radical and the radicals $R^5$ and $R^6$ each=$CH_3$.

2. The substituted pyrrole Mannich base according to claim 1, wherein the radical $R^1$ represents a $C_{1-6}$-alkyl radical.

3. The substituted pyrrole Mannich bases according to claim 1, wherein the radical $R^1$ represents an aryl, CN, Br, Cl or OH radical bonded via a $C_{1-3}$-alkylene group.

4. The substituted pyrrole Mannich bases according to claim 1, wherein the radical $R^1$ represents a phenyl, furoyl, thiophene or pyridine radical which is unsubstituted or at least monosubstituted by F, Cl, Br, $NH_2$, $NO_2$, $NH_2$—(C=S) or COOH.

5. The substituted pyrrole Mannich bases according to claim 1, wherein at least one of the radicals $R^3$, $R^{3'}$ or $R^{3''}$ represents H.

6. The substituted pyrrole Mannich bases according to claim 1, wherein at least one of the radicals $R^3$, $R^{3'}$ or $R^{3''}$ represents a $C_{1-6}$-alkyl radical.

7. The substituted pyrrole Mannich bases according to claim 1, wherein at least one of the radicals $R^3$, $R^{3'}$ or $R^{3''}$ represents an aryl radical bonded via a $C_{1-2}$-alkylene group.

8. The substituted pyrrole Mannich bases according to claim 1, wherein the radical $R^4$ represents an unsubstituted phenyl radical or a phenyl radical which is at least monosubstituted by methyl, tert-butyl, methoxy, F, Cl, Br or $CF_3$.

9. The substituted pyrrole Mannich bases according to claim 1, wherein at least one of the radicals $R^5$ and $R^6$ represents a saturated, unsubstituted or at least monosubstituted $C_{1-6}$-alkyl radical.

10. The substituted pyrrole Mannich bases according to claim 1, wherein the radicals $R^5$ and $R^6$ together denote $(CH_2)_n$, where n=4 or 5.

11. The substituted pyrrole Mannich bases according to claim 1, wherein the radical $R^7$ represents a $C_{1-6}$-alkyl radical.

12. The substituted pyrrole Mannich bases according to claim 1, wherein the radical $R^7$ represents an aryl radical bonded via a $C_{1-2}$-alkylene group.

13. The substituted pyrrole Mannich bases according to claim 1, wherein the radical $R^8$ represents a $C_{1-6}$-alkyl radical.

14. The substituted pyrrole Mannich bases according to claim 1, wherein the radical $R^8$ represents an aryl radical bonded via a $C_{1-2}$-alkylene group.

15. The substituted pyrrole Mannich bases according to claim 1, wherein the radical $R^9$ represents a $C_{1-6}$-alkyl radical.

16. The substituted pyrrole Mannich bases according to claim 1, wherein the radical $R^9$ represents an aryl radical bonded via a $C_{1-2}$-alkylene group.

17. The substituted pyrrole Mannich bases according to claim 1, wherein the radical $R^{10}$ represents a $C_{1-6}$-alkyl radical.

18. The substituted pyrrole Mannich bases according to claim 1, wherein the radical $R^{10}$ represents an aryl radical bonded via a $C_{1-2}$-alkylene group.

19. The substituted pyrrole Mannich bases according to claim 1, wherein the radical $R^{11}$ represents a $C_{1-6}$-alkyl radical.

20. The substituted pyrrole Mannich bases according to claim 1, wherein the radical $R^{11}$ represents an aryl radical bonded via a $C_{1-2}$-alkylene group.

21. The substituted pyrrole Mannich bases according to claim 1, wherein the radical $R^{12}$ represents a $C_{1-6}$-alkyl radical.

22. The substituted pyrrole Mannich bases according to claim 1, wherein the radical $R^{12}$ represents an aryl radical bonded via a $C_{1-2}$-alkylene group.

23. The substituted pyrrole Mannich bases according to claim 1, wherein the radical $R^{13}$ represents a $C_{1-6}$-alkyl radical.

24. The substituted pyrrole Mannich bases according to claim 1, wherein the radical $R^{13}$ represents an aryl radical bonded via a $C_{1-2}$-alkylene group.

25. The substituted pyrrole Mannich bases according to claim 1, wherein the radical $R^{14}$ represents a $C_{1-6}$-alkyl radical.

26. The substituted pyrrole Mannich bases according to claim 1, wherein the radical $R^{14}$ represents an aryl radical bonded via a $C_{1-2}$-alkylene group.

27. The substituted pyrrole Mannich bases according to claim 1, wherein the radical $R^{15}$ represents a $C_{1-6}$-alkyl radical.

28. The substituted pyrrole Mannich bases according to claim 1, wherein the radical $R^{15}$ represents an aryl radical bonded via a $C_{1-2}$-alkylene group.

29. The substituted pyrrole Mannich bases according to claim 1, wherein the pyrrole Mannich base is
- 4-[(2-methoxyphenyl)-(1-phenyl-1H-pyrrol-2-yl)methyl]-morpholine,
- 4-[[1-(2-fluorophenyl)-1H-pyrrol-2-yl]-(2-methoxyphenyl)methyl]-morpholine,
- 1-[(1-furan-2-yl-1H-pyrrol-2-yl)-(2-methoxyphenyl)methyl]-piperidine,
- 2[(2-methoxyphenyl)-pyrrolidin-1-yl-methyl]-1-phenyl-1H-pyrrole,
- 4-{2-[(2-methoxyphenyl)-piperidin-1-yl-methyl]-pyrrol-1-yl-methyl}-pyridine,
- 1(4-fluorophenyl)-2-[(2-methoxyphenyl)-pyrrolidin-1-yl-methyl]-1H-pyrrole,
- [(1-ethyl-1H-pyrrol-2-yl)-(2-methoxyphenyl)-methyl]dimethylamine,
- 3-(2-[dimethylamino-(2-methoxyphenyl)-methyl]-pyrrol-1-yl}-propionitrile,
- dimethyl-[phenyl-(1-phenyl-1H-pyrrol-2-yl)-methyl]amine,
- 2-[2-(dimethylaminophenylmethyl)-pyrrol-1-yl]phenylamine,
- [(1-benzyl-1H-pyrrol-2-yl)-phenyl-methyl]dimethylamine,
- 2-[2-(dimethylaminophenylmethyl)-pyrrol-1-yl]thiobenzamide,
- [(1-tert-butyl-1H-pyrrol-2-yl)-phenylmethyl]dimethylamine,
- 2-[2-(pyrrolidin-1-yl-o-tolylmethyl)-pyrrol-1-yl]-phenylamine,
- 1-methyl-2-(phenylpyrrolidin-1-yl-methyl)-1H-pyrrole,
- dimethyl-[(1-methyl-1H-pyrrol-2-yl)-phenylmethyl]amine, or
- 2-[2-(piperidin-1-yl-o-tolylmethyl)-pyrrol-1-yl]thiobenzamide,
- 2-[2-(dimethylamino-o-tolylmethyl)-pyrrol-1-yl]thiobenzamide,
- 2-[2-(phenylpyrrolidin-1-yl-methyl)-pyrrol-1-yl]thiobenzamide,
- 2-{2-[(2-methoxyphenyl)-pyrrolidin-1-yl-methyl]pyrrol-1-yl)-thiobenzamide,
- 2-{2-[(3,4-dimethoxyphenyl)-morpholin-4-yl-methyl]pyrrol-1-yl}-thiobenzamide,
- 3-{2-[(2-fluoro-phenyl)-piperidin-1-yl-methyl]-pyrrol-1-yl)-propionitrile,
- 2-[(4-bromo-phenyl)-pyrrolidin-1-yl-methyl]-1-phenyl-1H-pyrrole,
- 2-[2-(piperidin-1-yl-m-tolyl-methyl)-pyrrol-1-yl]phenylamine,
- 2-{2-[(4-bromo-2-fluoro-phenyl)-pyrrolidin-1-yl-methyl]-pyrrol-1-yl-methyl}-pyridine,
- 2-{2-[(3-phenoxy-phenyl)-piperidin-1-yl-methyl]pyrrol-1-yl-methyl}-pyridine,
- 2-{2-[(3-phenoxy-phenyl)-piperidin-1-yl-methyl]pyrrol-1-yl]-thiobenzamide,
- 1-[[1-(2-chloro-ethyl)-1H-pyrrol-2-yl]-(4-fluorophenyl)-methyl]-piperidine,
- 2-{2-[(3-phenoxy-phenyl)-piperidin-1-yl-methyl]pyrrol-1-yl}-ethanol,
- 3-[2-(piperidin-1-yl-m-tolyl-methyl)-pyrrol-1-yl]propan-1-ol,
- 3-{2-[(4-fluoro-phenyl)-piperidin-1-yl-methyl]-pyrrol-1-yl)-propan-1-ol,
- 1-[(4-fluoro-phenyl)-(1-methyl-1H-pyrrol-2-yl)methyl]-piperidine,
- 1-[(1-methyl-1H-pyrrol-2-yl)-(4-trifluoromethylphenyl)-methyl]-piperidine,
- 2-{2-[(2-chloro-6-fluoro-phenyl)-pyrrolidin-1-yl-methyl]-pyrrol-1-yl}-phenylamine,
- 2-{2-[(3-bromo-phenyl)-pyrrolidin-1-yl-methyl]-pyrrol-1-yl-methyl)-pyridine,
- 2-{2-[(3-bromo-4-fluoro-phenyl)-pyrrolidin-1-yl-methyl]-pyrrol-1-yl-methyl}-pyridine,
- 2-(2-[(2-chloro-6-fluoro-phenyl)-pyrrolidin-1-yl-methyl]-pyrrol-1-yl-methyl)-pyridine,
- 4-[(1-pyridin-2-yl-methyl-1H-pyrrol-2-yl)-pyrrolidin-1-yl-methyl]-benzonitrile,
- 2-[(3-bromo-4-fluoro-phenyl)-pyrrolidin-1-yl-methyl]-1-(4-fluoro-phenyl)-1H-pyrrole,
- 2-{2-[(5-bromo-2-fluoro-phenyl)-pyrrolidin-1-yl-methyl]-pyrrol-1-yl)-benzoic acid,
- 2-{2-[(5-bromo-2-fluoro-phenyl)-pyrrolidin-1-yl-methyl]-pyrrol-1-yl)-thiobenzamide or
- 1-tert-butyl-2-[(4-tert-butyl-phenyl)-pyrrolidin-1-yl-methyl]-1H-pyrrole.

30. A process for the preparation of one or more substituted pyrrole Mannich bases of formula I according to claim 1, said process comprising reacting one or more aromatic aldehyde compounds of formula II

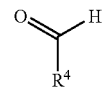

II wherein $R^4$ has the meaning according to formula I, in solution in the presence of a base with one or more secondary amines of formula III

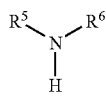

in which $R^5$ and $R^6$ have the meaning according to formula I, to give one or more aminal compounds of formula IV

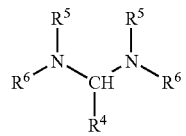

reacting said aminal compounds of formula IV, without further purification, with one or more acid chlorides in an absolute solvent to give one or more iminium salts of formula V

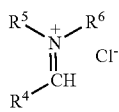

reacting said iminium salts of formula V, without further purification and in solution, with pyrrole and/or one or more substituted pyrrole compounds of formula VI

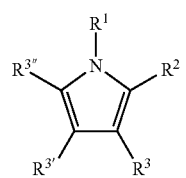

wherein $R^2$=H and the radicals $R^1$, $R^3$, $R^{3'}$, $R^{3''}$ and $R^7$ to $R^{15}$ have the meaning according to formula I, and purifying the so obtained pyrrole Mannich bases of formula I by washing and isolating by conventional methods.

31. The process according to claim 30, wherein the aromatic aldehyde compounds of formula II are reacted in an organic solvent, with the secondary amines of formula III.

32. The process according to claim 30, wherein the aromatic aldehyde compounds of formula II are reacted in the presence of potassium carbonate or boric acid anhydride with the secondary amines of formula III.

33. The process according to claim 30, wherein the aminal compounds of formula IV are reacted with acetyl chloride to give iminium salts of formula V.

34. The process according to claim 30, wherein the aminal compounds of formula IV are reacted in absolute diethyl ether to give iminium salts of formula V.

35. The process according to claim 30, wherein the iminium salts of formula V are reacted in acetonitrile with pyrrole and/or one or more substituted pyrrole compounds.

36. The process according to claim 30, wherein the pyrrole Mannich bases of formula I are purified by washing with acetone.

37. A medicament comprising at least one substituted pyrrole Mannich base of formula I

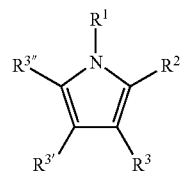

wherein
$R^1$=H, a $C_{1-10}$-alkyl, an aryl radical, a heteroaryl radical selected from the group consisting of furoyl, thiophene and pyridine radical, which is unsubstituted or at least monosubstituted by F, Cl, Br, $NH_2$, $NO_2$, $NH_2$—(C=S) or COOH, or
an aryl, said heteroaryl, CN, Br, Cl or OH radical bonded via a $C_{1-6}$-alkylene group,
$R^2$=CH($R^4$)N($R^5$)($R^6$),
$R^3$, $R^{3'}$, $R^{3''}$ are identical or different and are H, F, Cl, Br, $CF_3$, CN, $NO_2$, $SO_2NH_2$, $NHR^7$, $SR^8$, $OR^9$, CO($OR^{10}$), $CH_2$CO($OR^{11}$), $COR^{15}$, a $C_{1-10}$-alkyl, an aryl radical, or an aryl radical bonded via a $C_{1-6}$-alkylene group,
$R^4$=an unsubstituted phenyl radical or a phenyl radical which is at least monosubstituted by $C_{1-4}$-alkyl, $C_{1-3}$-alkoxy, halogen, $CF_3$, CN, O-phenyl or OH,
$R^5$, $R^6$ are identical or different and are a branched or unbranched, saturated or unsaturated, unsubstituted or at least monosubstituted $C_{1-6}$-alkyl radical or an unsubstituted or at least monosubstituted phenyl, benzyl or phenethyl radical,
or $R^5$ and $R^6$ together denote $(CH_2)_n$, where n=an integer from 3 to 6, or $(CH_2)_2O(CH_2)_2$,
$R^7$=H, $COR^{12}$, a $C_{1-10}$-alkyl, an aryl radical, or an aryl bonded via a $C_{1-6}$-alkylene group,
$R^8$=H, a $C_{1-10}$-alkyl, an aryl radical, or an aryl bonded via a $C_{1-6}$-alkylene group,
$R^9$=H, $COR^{13}$, a $C_{1-10}$-alkyl, an aryl radical, or an aryl bonded via a $C_{1-6}$-alkylene group,
$R^{10}$=H, a $C_{1-10}$-alkyl, an aryl radical, or an aryl bonded via a $C_{1-6}$-alkylene group,
$R^{11}$=H, a $C_{1-10}$-alkyl, an aryl radical, or an aryl bonded via a $C_{1-6}$-alkylene group,
$R^{12}$=a $C_{1-10}$-alkyl, an aryl radical, or an aryl bonded via a $C_{1-6}$-alkylene group,
$R^{13}$=a $C_{1-10}$-alkyl, an aryl radical, or an aryl bonded via a $C_{1-6}$-alkylene group,
$R^{14}$=H, a $C_{1-10}$-alkyl, an aryl radical, or an aryl bonded via a $C_{1-6}$-alkylene group,
$R^{15}$=$NHNH_2$, $NHR^{14}$, a $C_{1-10}$-alkyl, an aryl radical, or an aryl bonded via a $C_{1-6}$-alkylene group,
and/or racemates, enantiomers, or diastereomers thereof, and/or corresponding bases and/or corresponding salts of physiologically tolerated acids thereof.

38. The medicament according to claim 37, wherein said medicament comprises a mixture of enantiomers of at least one substituted pyrrole Mannich base of formula I, said mixture comprising the enantiomers in non-equimolar amounts.

39. The medicament according to claim 38, wherein the relative proportion of one of the enantiomers of the mixture is 5 to 45 mol %, based on the mixture of enantiomers.

40. The substituted pyrrole Mannich base according to claim 4, wherein the radical $R^1$ is a phenyl radical or a pyridine radical which is unsubstituted or at least monosubstituted by F or $NH_2-(C=S)$.

41. The substituted pyrrole Mannich base according to claim 8, wherein the radical $R^4$ represents an unsubstituted phenyl radical or a 2-methoxy-phenyl, 3-methoxy-phenyl, 4-methoxy-phenyl, 2-methyl-phenyl, 3-methyl-phenyl, 4-methyl-phenyl, 2-tert-butyl-phenyl, 3-tert-butyl-phenyl, 4-tert-butylphenyl, 2-fluoro-phenyl, 3-fluoro-phenyl, 4-fluoro-phenyl, 2-chloro-phenyl, 3-chloro-phenyl, 4-chloro-phenyl, 2-bromo-phenyl, 3-bromo-phenyl, 4-bromophenyl, 5-bromo-2-fluoro-phenyl, 2-chloro-4-fluorophenyl, 2-chloro-5-fluoro-phenyl, 2-chloro-6-fluorophenyl, 4-bromo-2-fluoro-phenyl, 3-bromo-4-fluorophenyl, 3-bromo-2-fluoro-phenyl, 2,3-dichlorophenyl, 2,4-dichloro-phenyl, 2,5-dichlorophenyl, 3,4-dichlorophenyl, 2,3-dimethyl-phenyl, 2,4-dimethyl-phenyl, 2,5-dimethylphenyl, 2,3-dimethoxy-phenyl, 2,4-dimethoxyphenyl, 2,5-dimethoxy-phenyl, 3,4-dimethoxyphenyl, 3,4,5-trimethoxy-phenyl, 2-trifluoromethyl-phenyl, 3-trifluoromethyl-phenyl or 4-trifluoromethyl-phenyl radical.

42. The substituted pyrrole Mannich base according to claim 8, wherein the radical $R^4$ represents an unsubstituted phenyl radical.

43. The substituted pyrrole Mannich base according to claim 9, wherein at least one of the radicals $R^5$ and $R^6$ is a $CH_3$ radical.

44. The process of claim 30, wherein the aromatic aldehyde compounds are reacted with the secondary amines at a temperature of from −10° C. to 110° C.

45. The process of claim 31, wherein the organic solvent is toluene.

46. The medicament of claim 37, wherein $R^1$ is a $C_{1-6}$-alkyl, phenyl, furoyl, thiophene or pyridine radical which is unsubstituted or at least monosubstituted by F, Cl, Br, $NH_2$, $NO_2$, $NH_2-(C=S)$ or COOH, or an aryl, CN, Br, Cl or OH radical bonded via a $C_{1-3}$-alkylene group.

47. The medicament of claim 37, wherein $R^1$ is a phenyl or a pyridine radical, which is unsubstituted or substituted by F or $NH_2-(C=S)$.

48. The medicament of claim 37, wherein $R^3$, $R^{3'}$, $R^{3''}$ are identical or different and are H, a $C_{1-6}$-alkyl radical or an aryl radical bonded via a $C_{1-2}$-alkylene group.

49. The medicament of claim 37, wherein $R^3$, $R^{3'}$, $R^{3''}$ are H.

50. The medicament of claim 37, wherein $R^4$ is an unsubstituted phenyl radical or a phenyl radical which is at least monosubstituted by methyl, tert-butyl, methoxy, F, Cl, Br or $CF_3$.

51. The medicament of claim 37, wherein $R^4$ is an unsubstituted phenyl radical or a 2-methoxy-phenyl, 3-methoxy-phenyl, 4-methoxy-phenyl, 2-methyl-phenyl, 3-methyl-phenyl, 4-methyl-phenyl, 2-tert-butyl-phenyl, 3-tert-butyl-phenyl, 4-tert-butylphenyl, 2-fluoro-phenyl, 3-fluoro-phenyl, 4-fluoro-phenyl, 2-chloro-phenyl, 3-chlorophenyl, 4-chlorophenyl, 2-bromo-phenyl, 3-bromo-phenyl, 4-bromophenyl, 5-bromo-2-fluoro-phenyl, 2-chloro-4-fluorophenyl, 2-chloro-5-fluoro-phenyl, 2-chloro-6-fluorophenyl, 4-bromo-2-fluoro-phenyl, 3-bromo-4-fluorophenyl, 3-bromo-2-fluoro-phenyl, 2,3-dichlorophenyl, 2,4-dichloro-phenyl, 2,5-dichlorophenyl, 3,4-dichlorophenyl, 2,3-dimethyl-phenyl, 2,4-dimethyl-phenyl, 2,5-dimethylphenyl, 2,3-dimethoxy-phenyl, 2,4-dimethoxyphenyl, 2,5-dimethoxy-phenyl, 3,4-dimethoxyphenyl, 3,4,5-trimethoxy-phenyl, 2-trifluoromethyl-phenyl, 3-trifluoromethyl-phenyl or 4-trifluoromethyl-phenyl radical.

52. The medicament of claim 37, wherein $R^4$ is an unsubstituted phenyl radical.

53. The medicament of claim 37, wherein $R^5$ and $R^6$ are identical or different and are a saturated, unsubstituted or at least monosubstituted $C_{1-4}$-alkyl radical.

54. The medicament of claim 37, wherein $R^5$ and $R^6$ are a $CH_3$ radical.

55. The medicament of claim 37, wherein $R^5$ and $R^6$ together are $(CH_2)_n$, where n=4 or 5.

56. The medicament of claim 37, wherein $R^7$ is a $C_{1-6}$-alkyl radical or an aryl radical bonded via a $C_{1-2}$-alkylene group.

57. The medicament of claim 37, wherein $R^8$ is a $C_{1-6}$-alkyl radical or an aryl radical bonded via $C_{1-2}$-alkylene group.

58. The medicament of claim 37, wherein $R^9$ is a $C_{1-6}$-alkyl radical or an aryl radical bonded via a $C_{1-2}$-alkylene group.

59. The medicament of claim 37, wherein $R^{10}$ is a $C_{1-6}$-alkyl radical or an aryl radical bonded via a $C_{1-2}$-alkylene group.

60. The medicament of claim 37, wherein $R^{11}$ is a $C_{1-6}$-alkyl radical or an aryl radical bonded via a $C_{1-2}$-alkylene group.

61. The medicament of claim 37, wherein $R^{12}$ is a $C_{1-6}$-alkyl radical or an aryl radical bonded via a $C_{1-2}$-alkylene group.

62. The medicament of claim 37, wherein $R^{13}$ is a $C_{1-6}$-alkyl radical or an aryl radical bonded via a $C_{1-2}$-alkylene group.

63. The medicament of claim 37, wherein $R^{14}$ is a $C_{1-6}$-alkyl radical or an aryl radical bonded via a $C_{1-2}$-alkylene group.

64. The medicament of claim 37, wherein $R^{15}$ is a $C_{1-6}$-alkyl radical or an aryl radical bonded via a $C_{1-2}$-alkylene group.

65. The medicament of claim 37, further comprising one or more active compounds and/or one or more auxiliary substances.

66. The medicament according to claim 39, wherein the relative proportion of one of the enantiomers of the mixture is 10–40 mol % based on the mixture of enantiomers.

67. A method for preparing a medicament, said method comprising mixing one or more of the substituted pyrrole Mannich bases of claim 1 with one or more pharmaceutically acceptable excipients or diluents.

68. A method comprising,
administering an effective amount of a composition comprising one or more of the pyrrole Mannich bases of claim 1 to a human in need of treatment for pain.

69. A method comprising,
administering an effective amount of a composition comprising one or more of the pyrrole Mannich bases of claim 1 to a human in need of treatment for allergic reaction.

70. A method comprising,
administering an effective amount of a composition comprising one or more of the pyrrole Mannich bases of claim 1 to a human in need of treatment for chronic pain.

71. A method comprising,
administering an effective amount of a composition comprising one or more of the pyrrole Mannich bases of claim 1 to a human in need of treatment for drug abuse.

72. A method comprising,
administering an effective amount of a composition comprising one or more of the pyrrole Mannich bases of claim 1 to a human in need of treatment for alcohol abuse.

73. A method comprising,
administering an effective amount of a composition comprising one or more of the pyrrole Mannich bases of claim 1 to a human in need of treatment for diarrhoea.

74. A method comprising,
administering an effective amount of a composition comprising one or more of the pyrrole Mannich bases of claim 1 to a human in need of treatment for inflammation.

75. A method comprising,
administering an effective amount of a composition comprising one or more of the pyrrole Mannich bases of claim 1 to a human in need of treatment for gastritis.

76. A method comprising,
administering an effective amount of a composition comprising one or more of the pyrrole Mannich bases of claim 1 to a human in need of treatment for ulcer.

77. A method comprising,
administering an effective amount of a composition comprising one or more of the pyrrole Mannich bases of claim 1 to a human in need of treatment for cardiovascular disease.

78. A method comprising,
administering an effective amount of a composition comprising one or more of the pyrrole Mannich bases of claim 1 to a human in need of treatment for urinary incontinence.

79. A method comprising,
administering an effective amount of a composition comprising one or more of the pyrrole Mannich bases of claim 1 to a human in need of treatment for depression.

80. A method comprising,
administering an effective amount of a composition comprising one or more of the pyrrole Mannich bases of claim 1 to a human in need of treatment for shock.

81. A method comprising,
administering an effective amount of a composition comprising one or more of the pyrrole Mannich bases of claim 1 to a human in need of treatment for migraine.

82. A method comprising,
administering an effective amount of a composition comprising one or more of the pyrrole Mannich bases of claim 1 to a human in need of treatment for narcolepsy.

83. A method comprising,
administering an effective amount of a composition comprising one or more of the pyrrole Mannich bases of claim 1 to a human in need of treatment for obesity.

84. A method comprising,
administering an effective amount of a composition comprising one or more of the pyrrole Mannich bases of claim 1 to a human in need of treatment for asthma.

85. A method comprising,
administering an effective amount of a composition comprising one or more of the pyrrole Mannich bases of claim 1 to a human in need of treatment for glaucoma.

86. A method comprising,
administering an effective amount of a composition comprising one or more of the pyrrole Mannich bases of claim 1 to a human in need of treatment for hyperkinetic syndrome.

87. A method comprising,
administering an effective amount of a composition comprising one or more of the pyrrole Mannich bases of claim 1 to a human in need of treatment for lack of drive.

88. A method comprising,
administering an effective amount of a composition comprising one or more of the pyrrole Mannich bases of claim 1 to a human in need of treatment for bulimia.

89. A method comprising,
administering an effective amount of a composition comprising one or more of the pyrrole Mannich bases of claim 1 to a human in need of treatment for anorexia.

90. A method comprising,
administering an effective amount of a composition comprising one or more of the pyrrole Mannich bases of claim 1 to a human in need of treatment for catalepsy.

91. A method comprising,
administering an effective amount of a composition comprising one or more of the pyrrole Mannich bases of claim 1 to a human in need of treatment for anxiolysis.

92. A method comprising,
administering an effective amount of a composition comprising one or more of the pyrrole mannich bases of claim 1 to a human in need of treatment to increase vigilance.

93. A method comprising,
administering an effective amount of a composition comprising one or more of the pyrrole mannich bases of claim 1 to a human in need of treatment to increase libido.

* * * * *